US012601712B2

(12) United States Patent (10) Patent No.: US 12,601,712 B2
Hansen (45) Date of Patent: Apr. 14, 2026

(54) SENSOR

(71) Applicant: Sensocure AS, Skoppum (NO)

(72) Inventor: Stein Ivar Hansen, Skoppum (NO)

(73) Assignee: SENSOCURE AS, Skoppum (NO)

( * ) Notice: Subject to any disclaimer, the term of this patent is extended or adjusted under 35 U.S.C. 154(b) by 805 days.

(21) Appl. No.: 17/432,208

(22) PCT Filed: Jan. 6, 2020

(86) PCT No.: PCT/EP2020/050147
    § 371 (c)(1),
    (2) Date: Aug. 19, 2021

(87) PCT Pub. No.: WO2020/169258
    PCT Pub. Date: Aug. 27, 2020

(65) Prior Publication Data
    US 2021/0389274 A1     Dec. 16, 2021

(30) Foreign Application Priority Data
    Feb. 21, 2019     (GB) ..................................... 1902361

(51) Int. Cl.
    *G01N 27/416*        (2006.01)
    *A61B 5/083*         (2006.01)
(52) U.S. Cl.
    CPC ........ *G01N 27/4162* (2013.01); *A61B 5/0836* (2013.01)

(58) Field of Classification Search
    CPC ........... G01N 27/4162; G01N 33/4925; G01N 27/02; G01N 27/04; G01N 27/4045;
    (Continued)

(56) References Cited

U.S. PATENT DOCUMENTS 4,474,183 A * 10/1984 Yano ................. G01N 27/4141
                                                 257/253
5,001,070 A * 3/1991 Ivaska ............... G01N 33/4925
                                                 436/127
(Continued)

FOREIGN PATENT DOCUMENTS

CN            2879181 A        3/2007
CN         107271409 A        10/2017
                (Continued)

OTHER PUBLICATIONS

Kawamoto et al., English translation of JPH0580010(A), 1993 (Year: 1993).*
(Continued)

*Primary Examiner* — James Lin
*Assistant Examiner* — Sommer Yousef Osman
(74) *Attorney, Agent, or Firm* — CANTOR COLBURN LLP

(57) ABSTRACT
The invention provides a physiological sensing device for the measurement of pCO2, the device comprising: (i) a closed chamber bounded, at least partially, by a carbon dioxide permeable membrane; and (ii) at least two electrodes within said chamber, wherein said chamber contains a substantially electrolyte-free liquid in contact with the electrodes and the membrane and wherein the liquid comprises at least one metal or metalloid ion.

20 Claims, 5 Drawing Sheets

(58) Field of Classification Search

CPC ............ A61B 5/0836; A61B 2562/168; A61B 5/14503; A61B 5/1473; A61B 5/14542

See application file for complete search history.

(56) References Cited

U.S. PATENT DOCUMENTS

| | | | | |
|---|---|---|---|---|
| 5,071,526 | A * | 12/1991 | Pletcher | ............. G01N 27/4045 |
| | | | | 205/781 |
| 6,248,224 | B1 * | 6/2001 | Kitzelmann | ....... G01N 33/0054 |
| | | | | 204/414 |
| 2005/0247574 | A1 * | 11/2005 | Varney | ................. G01N 33/004 |
| | | | | 204/431 |
| 2007/0175769 | A1 | 8/2007 | Hsiung et al. | |
| 2007/0227910 | A1 * | 10/2007 | Sommer | ............. G01N 27/127 |
| | | | | 204/431 |
| 2008/0011615 | A1 * | 1/2008 | Omtveit | ............... A61B 5/1473 |
| | | | | 205/777 |

FOREIGN PATENT DOCUMENTS

| | | | | |
|---|---|---|---|---|
| JP | H05-80010 | | 3/1993 | |
| JP | H0580010 | A * | 3/1993 | ............. G01N 27/08 |
| JP | H05312779 | A | 11/1993 | |
| JP | 2012042445 | A | 3/2012 | |
| WO | 0004386 | A2 | 1/2000 | |
| WO | 2006008505 | A1 | 1/2006 | |
| WO | 2020169258 | A1 | 8/2020 | |

OTHER PUBLICATIONS

Lin et al., Aqueous Li+/Al3+ alkaline solution for CO2 capture and the massive Li—Al—CO3 hydrotalcite precipitation during the interaction between CO2 gas and the Li+/Al3+ aqueous solution, 2013, Journal of Materials Chemistry A, 1, pp. 14773-14782. (Year: 2013).*

Li et al., Theoretical and experimental study of NH3suppression by addition of Me(II) ions (Ni, Cu and Zn) in an ammonia-based CO2 capture process, 2014, International Journal of Greenhouse Gas Control, 24, pp. 54-63. (Year: 2014).*

Solubility Rules, LibreTexts Chemistry, https://chem.libretexts.org/Bookshelves/Physical_and_Theoretical_Chemistry_Textbook_Maps/Supplemental_Modules_(Physical_and_Theoretical_Chemistry)/Equilibria/Solubilty/Solubility_Rules.*

Aluminum hydroxide, Sigma Aldrich, https://www.sigmaaldrich.com/US/en/product/sigald/239186.*

Copper (II) hydroxide, Sigma Aldrich, https://www.sigmaaldrich.com/US/en/product/aldrich/289787.*

Fasching et al., A miniaturized amperometric CO2 sensor based on dissociation of copper complexes, 2003, Sensors and Actuators B: Chemical, 93, 1-3, pp. 197-204 (Year: 2003).*

P27716CNPC—CN2020800159384—OA1 dated Nov. 30, 2023.

D1: Severinghaus J.W. et al., 'Electrodes for Blood pO2 and pCO2 Determination', Journal of Applied Physiology, Nov. 1958, vol. 13 Issue 3 pp. 515-520.

EP20700191-8—P27716EPPC—Communication under Rule 71(3) EPC dated Mar. 13, 2024.

International Search Report for International Application No. PCT/EP2020/050147; Application Filing Date: Jan. 6, 2020; Date of Mailing: Mar. 25, 2020; 3 pages.

Written Opinion for International Application No. PCT/EP2020/050147; Application Filing Date: Jan. 6, 2020; Date of Mailing: Mar. 25, 2020; 6 pages.

Written Opinion for Brazilian Application No. 112021016458, dated Sep. 18, 2025; 6 pages.

* cited by examiner

1

SENSOR

CROSS REFERENCE TO RELATED APPLICATIONS

This application is a National Stage application of PCT/EP2020/050147, filed Jan. 6, 2020, which claims the benefit of United Kingdom Application No. 1902361.3, filed Feb. 21, 2019, both of which are incorporated by reference in their entirety herein.

FIELD

The invention relates to a physiological sensor, in particular for the partial pressure of carbon dioxide ($pCO_2$), for example in vivo or ex vivo, e.g. in or on the surfaces of body tissues or organs. In particular, the invention relates to such a sensor which comprises metal or metalloid ions. The invention also relates to methods for measuring carbon dioxide partial pressure ($pCO_2$) using said sensor, and further to methods for amplifying the change in conductivity of a liquid in the presence of $CO_2$, said methods comprising adding at least one metal or metalloid ion to said liquid.

BACKGROUND

Ischemia is a medical term for a shortage of blood supply to an organ. If severe, it can lead to death of the affected tissue (infarction). A sensor can be provided to measure tissue $pCO_2$, which is a parameter that increases significantly during the early and reversible stages of ischemia. Such a sensor preferably provides the ability to identify the onset of ischemia events through real-time data.

Ischemia is the most prevalent cause of death in the western world. Thus, for example, myocardial infarction, cerebral infarction and other conditions characterised by hypoperfusion to one or more organs are major factors in mortality. Reperfusion, reversal of ischemia, is frequently possible if an ischemia is detected in time. Thus, early detection of ischemia followed by appropriate chemical treatment (e.g. with an agent such as streptokinase, urokinase or t-PA which serves to lyse thrombi or emboli) or surgical or radiological intervention can save the affected organ as well as the patient's life. While the heart may be monitored continuously for ischemia using an electrocardiograph (ECG), other organs may become severely ischemic and incur irreversible damage before any symptom is detected. Indeed many organs are "silent" when it comes to ischemia. The phenomenon of silent myocardial infarction is now well recognised. Furthermore, liver and kidney may be severely ischemic without alerting symptoms before the organ damage is irreversible.

It is known that there is a distinct correlation between $pCO_2$ in or on the surface of an organ and the presence of an ischemia in that organ. During tissue metabolic acidosis, e.g. during the anaerobic metabolism that occurs in an ischemia in any organ or tissue, large quantities of carbon dioxide are formed. $CO_2$ is in practical terms freely cell-membrane permeable and since in the ischemia blood flow to transport away the $CO_2$ is absent or restricted, $CO_2$ build up in the ischemic tissue will occur and $pCO_2$ in or on the ischemic tissue will increase. Generally, in the healthy body, the maximum $pCO_2$ in blood (venous blood) is 7-10 kPa and the maximum $pCO_2$ in healthy (aerobic) tissue is some 1-6 kPa higher, although the maxima may vary from organ to organ, e.g. 8-12 kPa for kidney, 7-11 kPa for liver, 8-12 kPa for intestinal serosa, and 12-19 kPa for intestinal mucosa. Where oxygen supply falls below the critical oxygen delivery level, $pCO_2$ values measured in the tissue may rise by 3 to 10 times and the elevated $pCO_2$ levels give a clear indication of anaerobic metabolism and hence, if appropriate, of ischemia.

A simple sensor particularly suitable for $pCO_2$ measurement, especially as part of a technique for monitoring for ischemias, is described in WO 00/04386. The sensor comprises a closed chamber bounded, at least partially, by a substantially water-tight, carbon dioxide-permeable membrane. The chamber contains at least two electrodes and a film of substantially electrolyte-free liquid, such as de-ionised water. The liquid contacts the membrane and both electrodes, so that carbon dioxide crossing the membrane increases the concentration of protons and bicarbonate ions in, and hence the conductivity of, the liquid. An improvement to this sensor, in which a non-ionic excipient is added to the liquid, is described in WO 2006/008505. The inclusion of this excipient enables osmolarity of the liquid to be controlled, thus avoiding potential errors in measurement under circumstances where there is a large osmotic pressure across the membrane.

However, limitations with such sensors still exist in terms of their sensitivity. Some targeted applications of the sensors require increased sensitivity and responsivity. This is for instance in tissue types where there are smaller increases in $pCO_2$ with the onset of ischemia, or where there is a desire for very early warning of slowly developing ischemia (decrease in vascular circulation developing over time, for instance in developing infections). Thus there remains a need to develop new sensors with increased sensitivity.

The present inventors have surprisingly found that the addition of at least one metal or metalloid ion to the liquid in the previously described sensors results in a significant increase in sensitivity to $CO_2$.

SUMMARY OF THE INVENTION

Thus, viewed from a first aspect, the invention provides a physiological sensing device for the measurement of $pCO_2$, the device comprising:
- (i) a closed chamber bounded, at least partially, by a carbon dioxide permeable membrane; and
- (ii) at least two electrodes within said chamber, wherein said chamber contains a substantially electrolyte-free liquid in contact with the electrodes and the membrane and wherein the liquid comprises at least one metal or metalloid ion.

In a second aspect, the invention provides a method for measuring $pCO_2$, said method comprising using a sensing device as hereinbefore defined.

In a further aspect, the invention provides the use of a sensing device as hereinbefore defined for measuring $pCO_2$.

In another aspect, the invention provides a method for measuring $pCO_2$, said method comprising the step of measuring the change in conductivity of a liquid in the presence of $CO_2$, wherein said liquid comprises at least one metal or metalloid ion.

In another aspect, the invention provides a method for amplifying the change in conductivity of a liquid in the presence of $CO_2$, said method comprising adding at least one metal or metalloid ion to said liquid.

DETAILED DESCRIPTION

The terms "sensing device" and "sensor" are used herein interchangeably and are intended to mean a device, module, or subsystem whose purpose is to detect events or changes in its environment and convert this into a 'signal' which can be read by an observer or by an instrument.

The device of the invention represents a development over prior art devices by way of the presence of at least one metal or metalloid ion in the liquid in the chamber. Thus, the liquid may comprise a mixture of more than one metal and/or metalloid ion, or only a single metal or metalloid ion is present.

Typical metal ions include any transition metal or a metal from Group 1, 2, 13 or 14 in the Periodic Table. It will be understood that the term "metalloid" used herein refers to a chemical element with properties intermediate between those of typical metals and non-metals. Example metalloids for use in the present invention include boron, silicon and germanium.

In one preferred embodiment, the metal and metalloid ions are selected from the group consisting of transition metals, Li, Na, Be, Mg, B, Al, Ga, In, Tl, Nh, Si, Ge, Sn, Pb and Fl.

Particularly preferred transition metals include Sc, Ti, V, Cr, Mn, Fe, Co, Ni, Cu, Zn, Y, Zr, Nb, Mo, Tc, Ru, Rh, Pd, Ag and Cd.

In another embodiment, the metal and metalloid ions are selected from the group consisting of Sc, Ti, V, Cr, Mn, Fe, Co, Ni, Cu, Zn, Y, Zr, Nb, Mo, Tc, Ru, Rh, Pd, Ag, Cd, B, Al, Ga, In, Tl and Nh.

A particularly preferred group of metal and metalloid ions for use in the present invention are Cr, Mn, Fe, Co, Ni, Cu, Zn, Pd, Ag, Cd, Al, Ga, In and Tl, especially Al, Ni, Ag, Cu, Co and Pd, such as Cu.

Where a mixture of metal and/or metalloid ions are present, one preferable embodiment is a mixture of Cu and Al ions. Another preferable mixture is Cu, Al and Ni ions.

The metal and metalloid ions may be in any oxidation state appropriate for each particular ion, however typically the ions are in a +2 or +3 oxidation state.

Typically, the metal or metalloid ions are generated in situ by the addition of an appropriate hydroxide, salt or complex of the required metal or metalloid ion(s). It follows naturally that since ions of the metal/metalloid are required for the present invention, the skilled person will be able to select appropriate hydroxides, salts and complexes which will dissociate to produce metal ions when added to the liquid (i.e. the hydroxide, salt or other complex is soluble in the liquid). It is particularly preferred if the metal and/or metalloid ions are provided in the form of a hydroxide.

Example salts include nitrates, oxides, carbonates, acetates and sulfates.

Example complexes include metal complexes comprise ligands such as carbon monoxide, carbon dioxide, water, nitrite and ammonia.

In one particular embodiment, the metal and/or metalloid ions may be provided in the form of a layered double hydroxide, preferably comprising Cu and Ni ions.

In an alternative embodiment, the metal and/or metalloid ions may be provided as isolated ions added directly to the liquid, typically in solution. Preferably this solution will comprise the same liquid as the liquid in the device, i.e. it is preferably an aqueous solution (e.g. comprises at least 80 wt % water) and especially preferably it is water, which is substantially electrolyte-free (i.e. de-ionised water).

In yet another embodiment the metal and/or metalloid ions are generated in situ from metal surfaces or interfaces present in the sensor, for example via chemical or electrochemical reactions involving one or more metals. One particular example is where the ions are electrocorrosion products resulting from the galvanic corrosion of a metal layer stack. In this scenario, two metals with sufficient separation in the galvanic series (e.g. >0.2), may be added to the sensor together with an electrolyte and the less noble metal will yield metal ions as corrosion products. This embodiment may also allow for the in situ provision of metal complexes as well as metal ions through the inclusion of different metal layers in the stack. For example, Pd and Cu can give rise to Cu ions and CuOH complexes, Au and Ni can give rise to Ni ions and NiOH complexes. The relative amounts of the ions/complexes generated may be dependent on factors such as pH and subjecting the system to a potential differential.

The concentration of the metal and/or metalloid ions in the liquid may be in the range 0.01 to 20 $mmolL^{-1}$, preferably 0.5 to 18 $mmolL^{-1}$, more preferably 0.1 to 15 $mmolL^{-1}$, even more preferably 0.25 to 12 $mmolL^{-1}$, such as 0.5 to 10 $mmolL^{-1}$.

Preferably, the liquid in contact with the electrodes is aqueous (e.g. comprises at least 80 wt % water) and especially preferably it is water, substantially electrolyte-free. By substantially electrolyte-free, it is meant that the liquid has an ionic osmolality no greater than that at 37° C. of an aqueous 5 mM sodium chloride solution, preferably no more than that of a 500 μM sodium chloride solution, more especially no more than that of a $10^{-5}$ to $10^{-6}$ M HCl solution. The substantially electrolyte free liquid when the liquid is water may also be termed de-ionised water.

Other solvents that react with $CO_2$ to increase or decrease their conductance, e.g. by the production or neutralization of ions, may likewise be used. In practice, however, deionized or distilled water has been found to function particularly well. In some embodiments, a strong acid (e.g. HCl) to a concentration of 0.1 to 100 preferably 0.5 to 50 μM, more especially about 1 μM, may be added to the deionized or distilled water. The function of this small addition of acid is generally to maintain the pH of the liquid at 6 or below to avoid significant contributions to conductance by hydroxyl ions and to maintain the linearity of the measurements of $pCO_2$. In other embodiments, a base may be added, in concentrations similar to those defined for the acid above. The purpose of the base is usually to correct for the acidification due to atmospheric $CO_2$.

In one embodiment of the invention, the liquid in the chamber may further comprise a non-ionic excipient. In this way, the osmolality of the liquid in the chamber can be increased to prevent egress of the liquid across the membrane, without affecting the electrical characteristics of the liquid. The excipient should have at least isotonic concentration, i.e. should be as osmotic with an aqueous solution of 0.9% w/v NaCl. Thus, the osmolality of the excipient in the chamber may be greater than that of 0.9% w/v aqueous NaCl, preferably greater than that of 1.8% w/v aqueous NaCl (twice isotonic concentration). Osmolalities greater than that of 4.5% w/v aqueous NaCl (five times isotonic concentration), or even greater than that of 9% w/v aqueous NaCl (ten times isotonic concentration) may be used.

Any suitable non-ionic excipient may be used that is inert to the proton and bicarbonate reaction in the chamber. The excipient should also be soluble in the liquid, for example water. The excipient is also desirably an accepted pharmaceutical excipient for intravenous use and with low viscosity for simple filling of the chamber. The excipient should preferably be sterilizable and storage stable. Desirably, the excipient should inhibit microbiological growth.

A suitable excipient is polyethylene glycol (PEG) and the presently preferred excipient is propylene glycol.

The primary components of the $pCO_2$ sensor of the invention are an electrode chamber, a $CO_2$ permeable membrane forming at least part of the wall of the electrode chamber, first and second electrodes having surfaces within said chamber (or providing internal surfaces to said chamber), and a liquid as defined above in the electrode chamber in contact with the membrane and the first and second electrodes. The sensor includes or is connectable to an AC power supply, a conductance (or resistance) determining device, a signal generator (which may be part of the determining means) and optionally a signal transmitter.

The mechanism by which $pCO_2$ is determined using the sensor device of the invention is straightforward. In a pure protic solvent, e.g. water, the electrical resistance is high because of the paucity of ionic species. Addition of $CO_2$ results in formation (with water) of $H^+$ and $HCO_3^-$ ions and thus a reduction in the electrical resistance. Since the only factor responsible for reduction in resistance in the sensor is $CO_2$ passing through the membrane, the change in resistance enables $pCO_2$ to be measured.

From the equilibrium constant for the $H_2O+CO_2$ to $H^++HCO_3^-$ equilibrium, $CO_2$ concentration is equal to $\alpha pCO_2$ (where a at 25° C. is 0.310). The electrical conductivity for protons is $G_{H+}=349.8$ S·cm$^2$/mol, that for hydroxyls is $G_{OH-}=198.3$ S·cm$^2$/mol and that for bicarbonate is $G_{HCO3-}=44.5$ S·cm$^2$/mol. The concentrations of $H^+$ and $OH^-$ vary inversely, and the concentrations of $H^+$ and $HCO_3^-$ are directly proportional to $pCO_2$. The total conductance of the solution is thus effectively proportional to $pCO_2$ since the contribution of OH– is minimal. The conductivity of the solution $G_{solution}$ is thus given by $$G_{solution}=\theta_{H+}[H^+]G_{H+}+\theta_{OH-}[OH^-]G_{OH-}+\theta_{HCO3-}[HCO_3^-]G_{HCO3-}$$

where $\theta_{H+}$, $\theta_{OH-}$ and $\theta_{HCO3-}$ are the activity coefficients for the three ionic species.

Table 1 below shows, by way of example, measured $pCO_2$ and pH values and corresponding calculated values for $H^+$, $OH^-$ and $HCO_3^-$ concentrations showing the increase of $H^+$ and $HCO_3^-$ with increasing $pCO_2$.

| Sample number | $pCO_2$ (kPa) | pH | $[H^+]$ (mmol/l) | $[OH^-]$ (mmol'l) | $[HCO_3^-]$ (mmol/l) |
| --- | --- | --- | --- | --- | --- |
| 1 | 6.38 | 5.141 | 7.23E−06 | 1.38E−09 | 7.23E−06 |
| 2 | 9.64 | 5.060 | 8.71E−06 | 1.15E−09 | 8.71E−06 |
| 3 | 15.37 | 4.891 | 1.29E−05 | 7.78E−10 | 1.29E−05 |
| 4 | 25.88 | 4.760 | 1.74E−05 | 5.75E−10 | 1.74E−05 |
| 5 | 31.48 | 4.664 | 2.17E−05 | 4.61E−10 | 2.17E−05 |

(pCO2 and pH measured with a standard blood gas analyser, AB L(R) System 625 at 37° C.).

The electrical conductivity is measured in the solvent film in the sensor of the invention. This can be done by applying a constant voltage (or current) to the electrodes and measuring the current (or voltage) changes which correspond to changes in conductivity as $CO_2$ enters the solvent through the membrane. Preferably however an alternating sine wave function voltage with a constant peak value is applied and the voltage drop across the electrodes is measured. The solution conductivity is then equal to the current passed through the electrode divided by the voltage drop across the electrodes.

The $pCO_2$ sensor may function by applying an alternating electrical potential to the electrodes whereby to cause an alternating current in the liquid. The liquid should be reactive with carbon dioxide to alter its conductance. The electrical potential may have a frequency of 20 to 100,000 Hz, preferably 100 to 10,000 Hz. The $pCO_2$ sensors of the invention are provided with or are connectable to an electrical power source arranged to apply an alternating electrical potential across the electrodes with a frequency of 100 to 10,000 Hz. The frequency is preferably greater than 1 kHz. The frequency is preferably less than 5 kHz, more preferably less than 2 kHz. At frequencies below 100 Hz, the sensitivity of pCO2 determination is lower due to electropolarization and moreover the instrument response time becomes overly slow, while at frequencies above 10 kHz sensitivity is again less due to the low impedance of the capacitances in the sensor.

The power source may be an AC power source or alternatively a DC source in conjunction with an oscillator, i.e. a combination which together constitutes an AC power source.

The power supply is preferably such that the maximum current density through the liquid at the electrodes is no more than 50 A/m$^2$, preferably no more than 30 A/m$^2$, more preferably no more than 20 A/m$^2$, in particular no more than 10 A/m$^2$, and most preferably about 1 A/m$^2$ or below. Higher current density values of 20 A/m$^2$ or greater should only be used at the higher frequencies, e.g. 1-10 kHz.

The smallest maximum current density is determined by detection limits, but values down to 10$^{-8}$ A/m$^2$ are usable. The smallest maximum current density however will generally be at least 0.1 μA/m$^2$.

By operating at such current densities and voltage frequencies, and by appropriate construction, the sensor can determine the conductance/resistance of the liquid into which the $CO_2$ migrates without any significant loss of accuracy arising as a result of the electropolarization of the electrodes.

For particularly high accuracy, the potential or current across the electrodes (and hence the resistance or conductance of the liquid between the electrodes) is determined using a lock-in amplifier set to the same frequency as that of the voltage generator or electrical power source.

Furthermore it is preferred to incorporate in the detection a high pass filter to screen out current with a frequency less than 100 Hz, preferably less than 150 Hz. The filter is preferably a passive filter, for example a capacitor and a resistor. The power source and the detector circuitry may, if desired, be included in the sensor of the invention, in this case, if it is desired that the sensor be wireless, it will preferably also be provided with means enabling the signal to be detected remotely, e.g. a transmitter, for example a RF transmitter. In this way the sensor may be implanted, for example in an at-risk patient. A further electrode may be provided that is electrically connected to the patient, for example to the patient's skin. The signal from this further electrode may be processed with the signal from the sensor in order to compensate for electromagnetic noise from the patient.

Electropolarization effects are considerably reduced by increasing the surface area of the electrodes in contact with the liquid, e.g. by siting the electrodes in wells disposed away from the plane of the membrane or by using nonplanar electrode surfaces, e.g. rough or textured surfaces. In general therefore it is desirable to have as large a ratio of surface area of electrode to liquid contact as possible, and as shallow as possible a liquid depth over as much as possible of its area of contact with the membrane. In this way the response time is reduced, electropolarization is reduced, lower frequencies may be used and stray capacitance effects are considerably reduced.

Increased electrical resistance relative to the resistance at the electrodes may be achieved by restricting the cross sectional area of the electrical path through the liquid between the electrodes at a zone in which the liquid is in contact with the membrane, e.g. by decreasing the depth of the liquid for a part of the path between the electrodes, and/or by ensuring a relatively large area of contact between each electrode and the liquid.

The resistance of the liquid at the membrane and between the electrodes may be increased by the use of structural elements to define liquid channels across the membrane between the electrodes, e.g. by disposing the membrane across or adjacent an insulating chamber wall portion in which such channels are formed, for example by etching. Likewise a porous spacer may be disposed between the membrane and the chamber wall to define the depth of the liquid.

Indeed, such spacers are important to use where, under the pressure conditions experienced in use, the membrane is sufficiently flexible and the liquid depth behind the membrane sufficiently small, for the measured conductance to vary with pressure.

In a preferred arrangement, the sensor comprises: a sensor body having a longitudinal axis; at least two electrodes spaced in a direction transverse to the longitudinal axis of the sensor body; a plurality of support members extending outwardly from the axis of the sensor body and defining between adjacent support members at least one liquid channel that provides a fluid pathway between the electrodes; and a gas-permeable membrane supported by the support members and providing an outer wall of the liquid channel(s).

This arrangement provides a compact configuration of the sensor with a longitudinal geometry that is suited to insertion in an organ. Furthermore, the support members are able to provide physical support to the membrane, as well as defining liquid channels of small cross-sectional area that allow accurate measurement.

In order to reduce the electropolarisation effect mentioned above, the electrodes may be located in a recess in the sensor body that has a greater cross-sectional area than the liquid channels. In this way, the current density around the electrodes is reduced by the greater volume for liquid.

The electrodes of the sensor may extend longitudinally, for example parallel to the longitudinal axis of the sensor body. Similarly, the liquid channel(s) may be transverse, for example perpendicular, to the longitudinal axis of the sensor body. In a preferred arrangement, the sensor comprises a plurality of liquid channels. For example, the sensor may comprise at least three liquid channels.

The support members may be transverse to the longitudinal axis of the sensor body. For example, the support members may be perpendicular to the longitudinal axis of the sensor body in the circumferential direction. In a preferred arrangement, the support members are in the form of rings formed about the longitudinal axis of the sensor body. The cross-section of the support members may be any suitable shape. It has been found in particular that support members with a substantially triangular, in particular sawtooth, cross-section are particularly easily formed by injection moulding. Alternatively, a substantially rectangular cross-section may be used. The support members may be formed integrally with the sensor body, for example by injection moulding. The sensor preferably comprises at least four support members. The sensor body and/or the sensor may be generally cylindrical. The membrane may be arranged to surround the sensor body.

The described geometry may be applied to any suitable sensor. In the preferred arrangement, the sensor is a $pCO_2$ sensor.

Where the sensor is constructed with the liquid film in place, the electrodes are preferably of, or plated with, an inert material such that the resistivity of the liquid will not change significantly with storage. Suitable materials include platinum (especially black platinum), gold, silver, aluminium and carbon. Gold is particularly preferred. In general inert electrodes which do not generate solvated ions are preferred.

The membrane may be any material which is permeable to $CO_2$, and substantially impermeable to the solvent of the liquid, any electrolyte and water. Polytetrafluoroethylene, e.g. Teflon®, silicone rubber, polysiloxane, polyolefins or other insulating polymer films may be used, e.g. at thicknesses of 0.5 to 250 μm. The thicker the membrane, in general the slower the response time of the sensor will be. However the thinner the membrane the greater the risk of non-uniformities or of perforation or other damage. Conveniently however the thickness of the membrane will be 1 to 100 μm, preferably 50 to 100 μm.

The walls of the chamber of the sensor of the invention may be of any suitable material, e.g. plastics. Preferably the material should be capable of withstanding conditions normally used in sterilisation, e.g. radiation sterilization (for example using gamma radiation) or thermal sterilization (for example using temperatures of about 121° C. as used in autoclave sterilisation). In the case of thermal sterilization, the liquid will generally be sterile filled into the sensor after sterilization. The walls of the chamber and the membrane may be of the same material, e.g. Teflon®, machined to have self-supporting walls and a thinner gas-permeable membrane. The sensors of the invention are generally relatively inexpensive and so, unlike prior art sensors, may be single-use devices. Moreover the electrode chamber can be made extremely small without difficulty (unlike the prior art glass electrode containing sensors for which miniaturization poses insuperable impedance problems). This arrangement provides a sensor, in particular, a $pCO_2$ sensor, which can be inserted easily into the tissue of an animal, including a human, which can be retained in the tissue during monitoring and which can be removed easily when monitoring is complete.

The device is sufficiently small that it will not cause undue disturbance to the tissue to be monitored. Consequently, the device may have a maximum diameter of 2 mm, preferably 1 mm. The sensors according to the invention are readily produced having a size and configuration particularly suited to measuring $pCO_2$ on the surface of or in an organ, duct or tissue, e.g. brain, heart, liver, kidney, gut or muscle. This is of particular interest as it allows the functioning of the organ, duct or tissue to be monitored, e.g. during and after transplant, in intensive care, following injury, etc. and so allows early detection of ischemias.

The partial pressure determined by the sensor may be a quantified value or it may simply be an indication that $pCO_2$ is above or below one or more threshold values indicative of ischemia or non-ischemia, values which may be varied according to the location of the $pCO_2$ measurement site.

The sensor may be used for a single measurement of $pCO_2$ or, more preferably, may be used for continuous or repeated monitoring, especially of an at-risk patient, for example a patient in intensive care, undergoing or recovering from an organ or tissue transplant operation, assessed as having unstable angina, recovering from a coronary artery bypass operation, suffering trauma (e.g. of skeletal muscle), or suffering from hypovolemia (e.g. shock).

The device may comprise a plurality of sensors for respective physiological parameters. For example, the device may comprise an array of sensors. Such sensors may measure one or more of the partial pressures of carbon dioxide, the partial pressure of oxygen, temperature, pH or glucose concentration, for example. In the presently preferred embodiment, the device comprises a temperature sensor and a pCO2 sensor.

The invention further relates to a method for measuring $pCO_2$, said method comprising using a sensor as hereinbefore defined. In another aspect, the invention provides a method for measuring $pCO_2$, said method comprising the step of measuring the change in conductivity of a liquid in the presence of $CO_2$, wherein said liquid comprises at least one metal or metalloid ion.

The invention also relates to the use of a sensor as hereinbefore defined for measuring $pCO_2$.

In another aspect, the invention relates to a method for amplifying the change in conductivity of a liquid in the presence of $CO_2$, said method comprising adding at least one metal or metalloid ion to said liquid. In all these embodiments, the liquid and metal/metalloid ions may be defined as previously described in the context of the sensor.

The invention will now be described further with reference to the following non-limiting examples and figures.

EXAMPLES

Example 1

Figure 1:
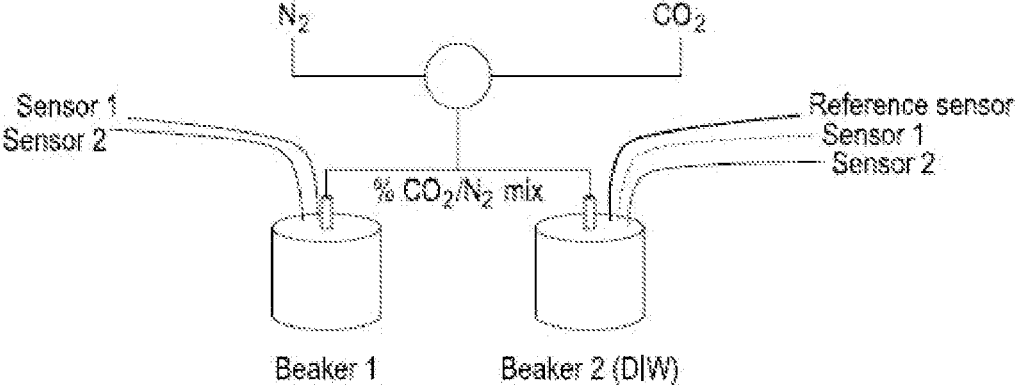
FIG. 1: Schematic diagram of experimental set-up for Example 1

The experimental set-up shown in FIG. 1 was constructed. A gas mixture of $CO_2$ and $N_2$ was bubbled through diffusers into de-ionised water. The composition of the mixture was controlled by two computer controlled mass flow controllers. Two 40 mL beakers were filled with de-ionised water at ambient temperature. Each beaker contained a gas diffuser and two sensors (one each of type S1 and S2). Beaker 2 also contained a reference sensor. Sensors S1 and S2 comprised of gold stripe electrodes located diametrically opposed on the outside of a cylindrical polymer carrier substrate. S2 electrode spacing approximately 0.7 mm, lengths 5 mm, S1 spacing approximately 1.7 mm, electrode lengths 10 mm. The reference sensor consisted of two 10 mm cylindrical steel electrodes 175 um diameter, suspended 1 mm apart. The sensors were connected to a PC through an analogous digital converter and conditioning electronics.

Figure 2:
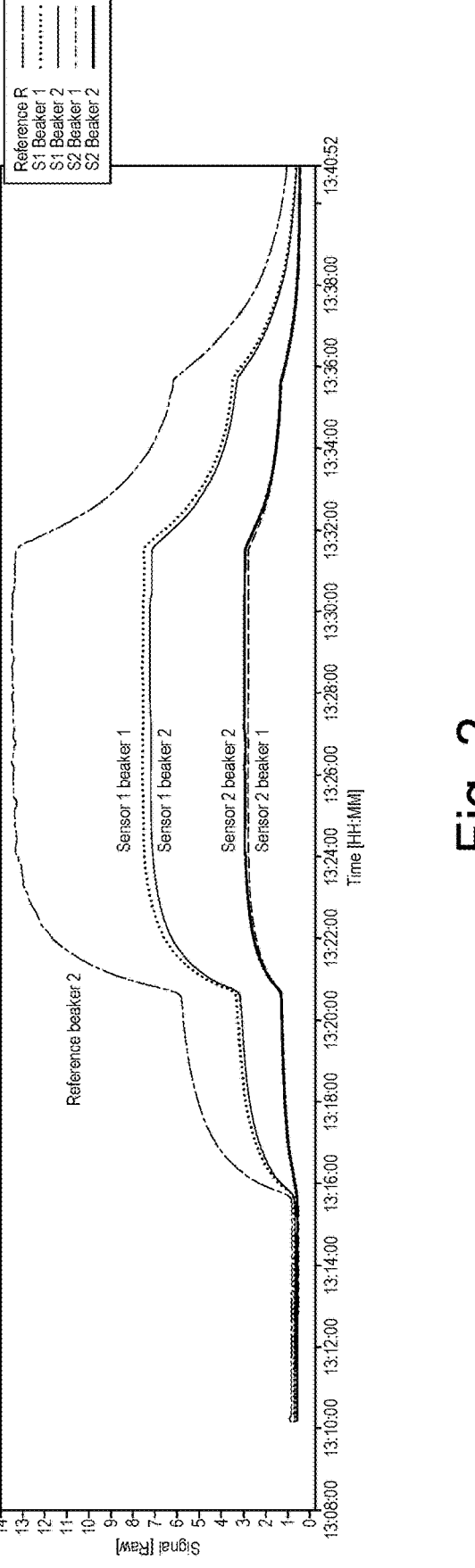
FIG. 2: $CO_2$ detection prior to addition of metal ions

The gas mixture composition was varied with time following the sequence O % $CO_2$, 6% $CO_2$, 10% $CO_2$, 14% $CO_2$, 6% $CO_2$ and 0% $CO_2$ over a time period of 30 minutes and the response of the sensors followed. The Results are shown in FIG. 2.

Figure 3:
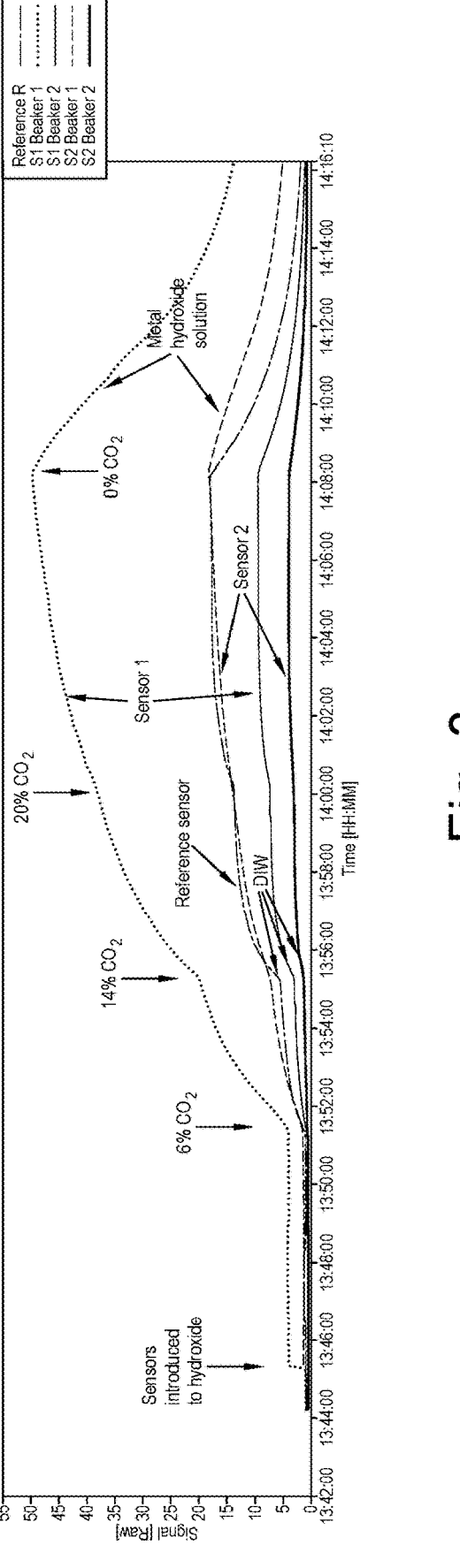
FIG. 3: $CO_2$ detection after addition of CuOH

Copper hydroxide (2.5 mmolL$^{-1}$) was then added to Beaker 1 and the gas mixture composition was varied with time following the sequence O % $CO_2$, 6% $CO_2$, 14% $CO_2$, 20% $CO_2$ and 0% $CO_2$ over a time period of 30 minutes and the response of the sensors followed. The Results are shown in FIG. 3. The signal can be seen to increase significantly for Sensors 1 and 2 in Beaker 1 with the metal ions present compared to Sensors 1 and 2 in Beaker 2 which contains only de-ionised water. Sensitivity to $CO_2$ is shown to increase by a factor up to around 9 on addition of the metal hydroxide.

Example 2

Figure 4:
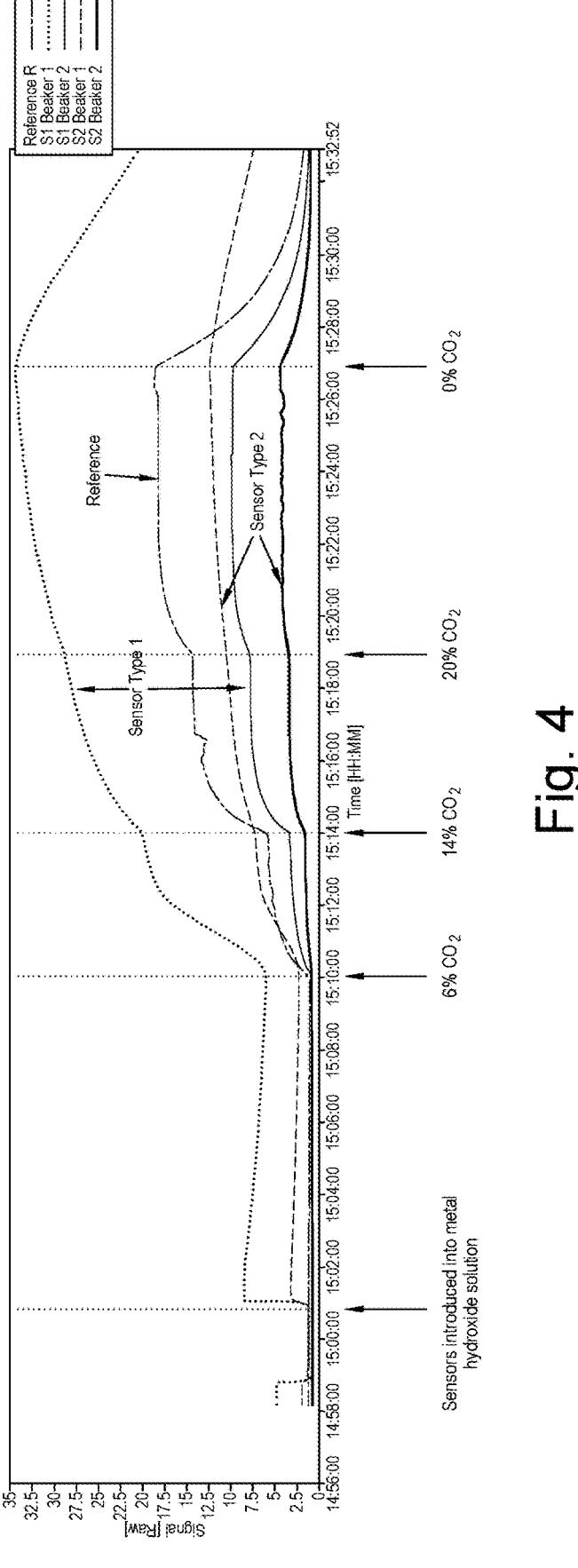
FIG. 4: CO2 detection after addition of AlOH and CuOH

The same experiment as described in Example 1 was repeated, except that a 1:1 ratio of AlOH (3.2 mmolL$^{-1}$) and CuOH (2.5 mmolL$^{-1}$) were added to Beaker 1 and the gas mixture composition was varied with time following the sequence 0% 6% $CO_2$, 10% $CO_2$, 14% $CO_2$, 20% $CO_2$, 6% $CO_2$ and 0% $CO_2$ over a time $CO_2$, period of 30 minutes and the response of the sensors followed. The Results are shown in FIG. 4. Again, the signal can be seen to increase significantly for Sensors 1 and 2 in Beaker 1 with the metal ions present compared to Sensors 1 and 2 in Beaker 2 which contains only de-ionised water.

Example 3

The effects of changing the metal ion and concentration on the increase in sensitivity were investigated using the same set-up described for Example 1. The results are shown in FIGS. 5 and 6.

Figure 5:
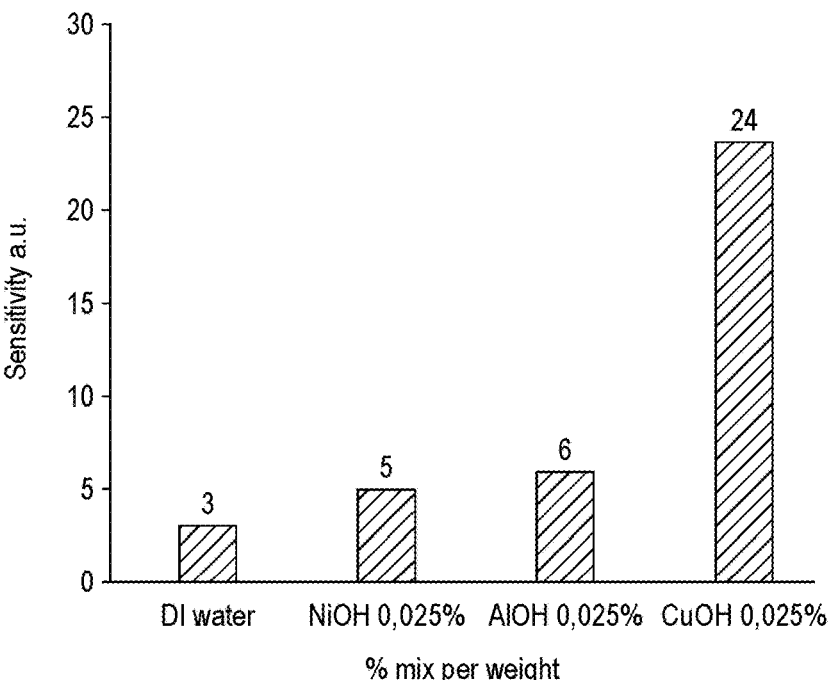
FIG. 5: Relationship between sensitivity and metal ion

FIG. 5 shows that all of NiOH, AlOH and CuOH give an increase in sensitivity to $CO_2$ measurement when added to de-ionised water, with CuOH showing the highest increase. The concentrations of NiOH, AlOH and CuOH were 2.7 mmolL$^{-1}$, 3.21 mmolL$^{-1}$ and 2.56 mmolL$^{-1}$, respectively.

Figure 6:
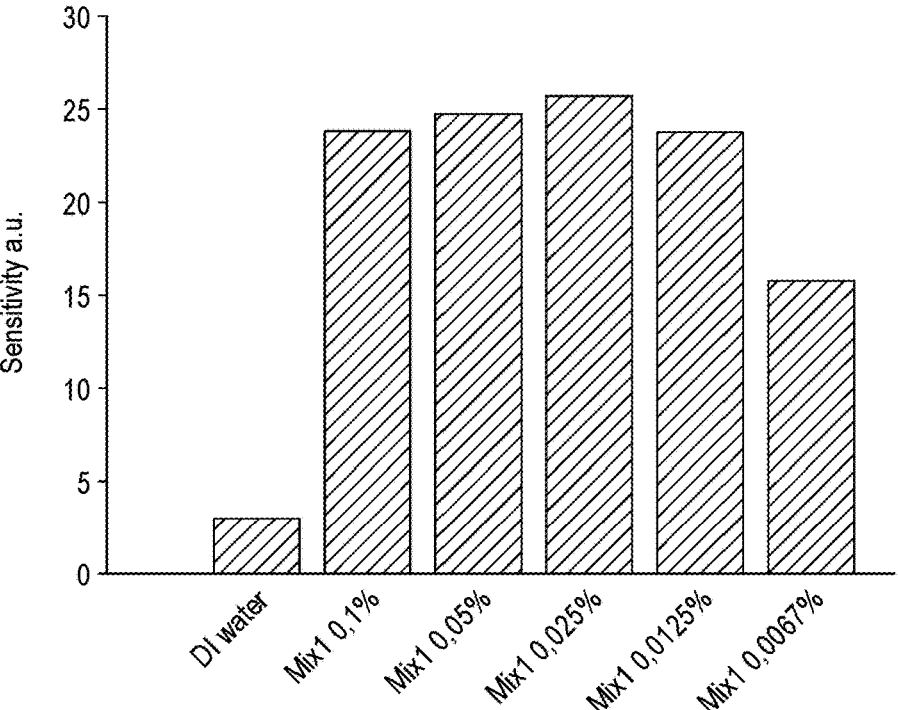
FIG. 6: Relationship between sensitivity and concentration

FIG. 6 shows that a significant increase in sensitivity is observed for a mixture of CuOH, AlOH and NiOH over a wide concentration range. Mix1 at 0.1% contains NiOH, AlOH and CuOH at concentrations of 10.24 mmolL$^{-1}$, 12.84 mmolL$^{-1}$ and 10.8 mmolL$^{-1}$, respectively. The concentrations were decreased by a factor of two each time, thus Mix1 at 0.05% contains NiOH, AlOH and CuOH at half the concentration of Mix1 at 0.1% and so on.

The invention claimed is:

1. A physiological sensing device for a measurement of $pCO_2$, the sensing device comprising:
   (i) a closed chamber bounded, at least partially, by a carbon dioxide permeable membrane; and
   (ii) at least two electrodes within said chamber,
   wherein said chamber contains a substantially electrolyte-free liquid in contact with the at least two electrodes and the membrane and wherein the liquid comprises at least one metal or metalloid ion, wherein the at least one metal or metalloid ion comprises Cu, and wherein if the at least one metal or metalloid ion is provided in a form of a metal complex comprising ligands, then the ligands are selected from carbon monoxide, carbon dioxide, water, nitrite and ammonia; and
   wherein the substantially electrolyte-free liquid has an ionic osmolality no greater than that at 37° C. of an aqueous 5 mM sodium chloride solution.

2. The sensing device as claimed in claim 1, wherein a mixture of metal and/or metalloid ions are present.

3. The sensing device as claimed in claim 2, wherein the mixture of metal and/or metalloid ions is a mixture of Cu and Al ions.

4. The sensing device as claimed in claim 1, wherein a concentration of the at least one metal and/or metalloid ions is in a range 0.01 to 20 mmolL$^{-1}$.

5. The sensing device as claimed in claim 1, wherein the at least one metal or metalloid ion is provided in a form of copper hydroxide.

6. The sensing device as claimed in claim 1, wherein the liquid comprises water.

7. The sensing device as claimed in claim 6, wherein the liquid is de-ionised water.

8. A method for measuring pCO$_2$, said method comprising using the sensing device as defined in claim 1.

9. The sensing device as claimed in claim 1, wherein the at least one metal or metalloid ion is provided in a form of copper nitrate.

10. The sensing device as claimed in claim 1, wherein the at least one metal or metalloid ion is provided in a form of copper oxide.

11. The sensing device as claimed in claim 1, wherein the at least one metal or metalloid ion is provided in a form of copper sulfate.

12. The sensing device as claimed in claim 1, wherein the at least one metal or metalloid ion is provided in a form of copper carbonate.

13. The sensing device as claimed in claim 1, wherein the at least one metal or metalloid ion is provided in a form of copper acetate.

14. The sensing device as claimed in claim 1, wherein the at least one metal or metalloid ion is provided in the form of the metal complex comprising ligands, wherein the ligands are carbon monoxide.

15. The sensing device as claimed in claim 1, wherein the at least one metal or metalloid ion is provided in the form of the metal complex comprising ligands, wherein the ligands are carbon dioxide.

16. The sensing device as claimed in claim 1, wherein the at least one metal or metalloid ion is provided in the form of the metal complex comprising ligands, wherein the ligands are water.

17. The sensing device as claimed in claim 1, wherein the at least one metal or metalloid ion is provided in the form of the metal complex comprising ligands, wherein the ligands are nitrite.

18. The sensing device as claimed in claim 1, wherein the at least one metal or metalloid ion is provided in the form of the metal complex comprising ligands, wherein the ligands are ammonia.

19. A method for measuring pCO$_2$, said method comprising a step of measuring a change in conductivity of a substantially electrolyte-free liquid in a presence of CO$_2$, wherein said liquid comprises at least one metal or metalloid ion, wherein the at least one metal or metalloid ion comprises Cu, and wherein if the at least one metal or metalloid ion is provided in the form of a metal complex comprising ligands, then the ligands are selected from carbon monoxide, carbon dioxide, water, nitrite and ammonia; and wherein the substantially electrolyte-free liquid has an ionic osmolality no greater than that at 37° C. of an aqueous 5 mM sodium chloride solution.

20. A method for amplifying a change in conductivity of a substantially electrolyte-free liquid in a presence of CO$_2$, said method comprising adding at least one metal or metalloid ion to said liquid, wherein the at least one metal or metalloid ion comprises Cu, and wherein if the at least one metal or metalloid ion is provided in a form of a metal complex comprising ligands, then the ligands are selected from carbon monoxide, carbon dioxide, water, nitrite and ammonia; and wherein the substantially electrolyte-free liquid has an ionic osmolality no greater than that at 37° C. of an aqueous 5 mM sodium chloride solution.

* * * * *